US00PP11924P2

(12) United States Plant Patent
Trees

(10) Patent No.: US PP11,924 P2
(45) Date of Patent: Jun. 12, 2001

(54) NEW GUINEA IMPATIENS PLANT NAMED 'BALCELROST'

(75) Inventor: Scott C. Trees, Nipomo, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,967

(22) Filed: Dec. 31, 1999

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Balcelrost', characterized by its red and purple bi-colored flowers; upright and mounded plant habit; good basal branching; and dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name Balcelrost.

The new Impatiens is a product of a planned breeding program conducted by the Inventor in Arroyo Grande, Calif. The objective of the breeding program was to develop new cultivars with freely-branching growth habit, numerous large flowers, and attractive flower and foliage colors.

The new Impatiens originated from a cross made by the Inventor of a proprietary selection of *Impatiens hawkeri* identified as code number 64NG670 as the male, or pollen parent, with the *Impatiens hawkeri* cultivar Guadeloupe, disclosed in U.S. Plant Pat. No. 10,001 as the female, or seed parent. The cultivar Balcelrost was discovered and selected by the Inventor as a flowering plant within the progeny of the stated cross in a controlled environment in Arroyo Grande, Calif. in 1997.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balcelrost'. These characteristics in combination distinguish 'Balcelrost' as a new and distinct cultivar:

1. Red and light pink bi-colored flowers.
2. Upright and mounded plant habit.
3. Good basal branching.
4. Dark green leaves.

The new Impatiens can be compared to the female parent, the cultivar Guadeloupe. However, in side-by-side comparisons conducted by the Inventor in Arroyo Grande, Calif., plants of the new Impatiens differ from plants of the cultivar Guadeloupe in the following characteristics:

1. Plants of the new Impatiens have shorter internodes than plants of the cultivar Guadeloupe.
2. Plants of the new Impatiens have slightly smaller flowers and shorter peduncles than plants of the cultivar Guadeloupe.
3. Flower color of plants of the new Impatiens is more red than flower color of plants of the cultivar Guadeloupe.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Impatiens. The photograph comprises a top perspective view of a typical flowering plant of 'Balcelrost'.

DETAILED BOTANICAL DESCRIPTION

The cultivar Balcelrost has not been observed under all possible environmental conditions. The phenotype may vary somewhat with variations in environment such as temperature and light intensity, without, however, any variance in genotype. The following observations and measurements describe plants about 10 weeks from rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 foot-candles.

In the following description, color references are made to The Royal Horticultural Society Colour Chart except where general terms of ordinary dictionary significance are used.

Botanical classification: *Impatiens hawkeri* cultivar Balcelrost.

Parentage:

*Male parent.*—Proprietary selection of *Impatiens hawkeri* identified as 64NG670, not patented.

*Female parent.*—*Impatiens hawkeri* cultivar Guadeloupe, disclosed in U.S. Plant Pat. No. 10,001.

Propagation:

*Type cutting.*—Terminal cuttings.

*Time to initiate roots.*—About 7 days with 18° C.

*Time to develop roots.*—About 21 days with 18° C.

*Root description.*—Fibrous, fine, freely branching.

Plant description:

*Plant form.*—Upright and mounded.

*Growth and branching habit.*—Moderately vigorous. Good basal branching, dense and bushy growth. Appropriate for 10 and 12.5-cm containers.

*Crop time.*—About 8 to 10 weeks are required to produce a finished flowering plant from a rooted cutting.

*Plant height.*—About 16.3 cm.

*Plant diameter.*—About 27.4 cm.

*Lateral branches.*—Diameter: About 5 mm. Internode length: About 1.8 cm. Color: 187B.

*Foliage description.*—Leaves simple, generally symmetrical, abundant, in whorls or opposite. Length: About 9.4 cm. Width: About 3 cm. Shape: Lanceolate. Apex: Acuminate. Base: Cuneate. Margin: Serrulate with ciliation. Texture: Slightly rough, glabrous. Color: Fully expanded leaves, upper surface: Darker than 139A. Fully expanded leaves, lower surface: 183A. Venation, upper surface: 187C. Venation, lower surface: 187B. Petiole: Length: About 2 cm. Diameter: About 3 mm. Color: 187C.

Flower description:

*Flower type and habit.*—Red and purple bi-colored flowers. Freely and continuously flowering; about 3 flowers per lateral stem. Flowers arise from leaf axils. Flowers positioned mostly above the foliage and typically face upright. Flowers roughly rounded in shape. Flowers persistent.

*Flowering season.*—Year-round under greenhouse conditions. In the garden, flowering is continuous from spring until fall.

*Flower buds.*—Length: About 1.7 cm. Diameter: About 1.3 cm. Shape: Ovoid. Color: Close to 53C.

*Flower size.*—Diameter: About 6 cm. Depth: About 1.2 cm.

*Petals.*—Quantity: Five, imbricate. Length: About 3.1 cm. Width: About 3.9 cm. Shape: Obovate to obcordate. Apex: Emarginate. Base: Attenuate. Margin: Entire. Texture: Smooth. Color: Fully opened, upper surface: Background, between 74B and 78B; central longitudinal stripes, close to 53C, center strip on upper petal is broader than stripes on other petals, iridescent. Fully opened, lower surface: 46D.

*Spur.*—Length: About 4.4 cm. Shape: Narrow and curved. Color: Base, 184B; towards apex, 151A.

*Peduncles.*—Length: About 5 cm. Angle: Erect. Strength: Strong. Color: Close to 152C.

*Reproductive organs.*—Androecium: Stamen number: Five, anthers fused, filaments free. Anther shape: Obovate. Anther length: About 3 mm. Anther color: 158B. Amount of pollen: Moderate. Pollen color: 158C. Gynoecium: Five-loculate fused. Pistil length: About 3 mm. Style color: 183B. Ovary color: 183A.

Disease resistance: Under commercial conditions, resistance to pathogens common to New Guinea Impatiens has not been observed.

Seed development: Seed production has not been observed.

It is claimed:

1. A new and distinct cultivar of New Guinea Impatiens plant named 'Balcelrost', as illustrated and described.

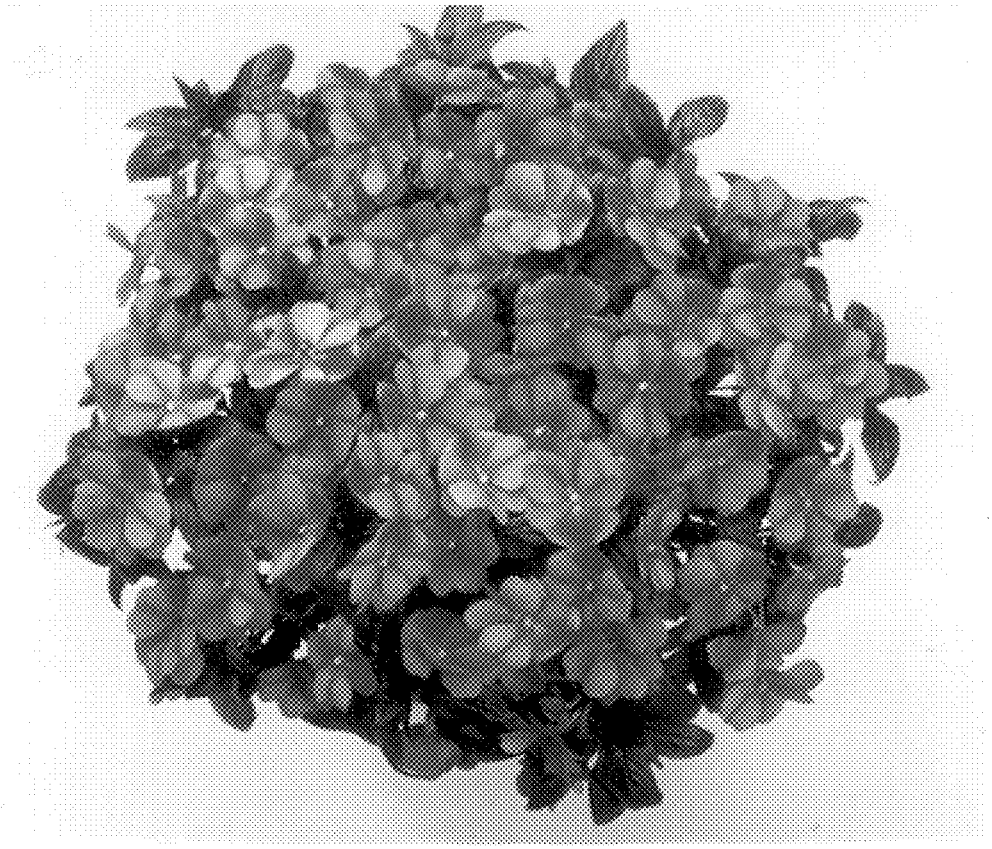

* * * * *